(12) United States Patent
Candau

(10) Patent No.: US 7,364,720 B2
(45) Date of Patent: *Apr. 29, 2008

(54) PHOTOSTABILIZATION OF DIBENZOYLMETHANE UV-SCREENING AGENTS WITH ARYLALKYL BENZOATE COMPOUNDS/AMIDE-BASED OILS AND PHOTOPROTECTIVE COMPOSITIONS COMPRISED THEREOF

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 325 days.

This patent is subject to a terminal disclaimer.

(21) Appl. No.: 11/172,902

(22) Filed: Jul. 5, 2005

(65) Prior Publication Data

US 2006/0002873 A1 Jan. 5, 2006

Related U.S. Application Data

(60) Provisional application No. 60/589,010, filed on Jul. 20, 2004.

(30) Foreign Application Priority Data

Jul. 2, 2004 (FR) .................................. 04 51417

(51) Int. Cl.
A61Q 17/04 (2006.01)
A61Q 17/00 (2006.01)
A61Q 19/04 (2006.01)
A61Q 19/00 (2006.01)
A61K 8/02 (2006.01)

(52) U.S. Cl. .............................. 424/59; 60/400; 60/401
(58) Field of Classification Search .................. 424/59, 424/60, 400, 401
See application file for complete search history.

(56) References Cited

U.S. PATENT DOCUMENTS

| 5,672,337 | A | 9/1997 | Ascione et al. |
| 5,849,273 | A | 12/1998 | Bonda et al. |
| 7,132,097 | B2 | 11/2006 | Bertz et al. |
| 2003/0044365 | A1 | 3/2003 | Candau |
| 2005/0152858 | A1 | 7/2005 | Bertz et al. |
| 2006/0067900 | A1 | 3/2006 | Bertz et al. |
| 2006/0067901 | A1 | 3/2006 | Bertz et al. |

FOREIGN PATENT DOCUMENTS

| EP | 0 717 982 A1 | 6/1996 |
| EP | 0 815 834 A1 | 1/1998 |
| FR | 2727861 A1 | 12/1994 |
| FR | 2 800 991 A1 | 5/2001 |
| FR | 2800991 A1 | 5/2001 |
| FR | 2827511 A1 | 7/2001 |
| JP | 8-225436 | 9/1996 |
| JP | 2003/55181 A | 2/2003 |
| WO | WO 03/039510 A1 | 5/2003 |
| WO | WO 2005/009341 | 2/2005 |
| WO | WO 2005/069822 A2 | 8/2005 |
| WO | WO 2005/117823 A1 | 12/2005 |
| WO | WO 2005/117824 A1 | 12/2005 |
| WO | WO 2005/117825 A1 | 12/2005 |
| WO | WO 2006/009828 A1 | 1/2006 |
| WO | WO 2006/041506 A2 | 4/2006 |

OTHER PUBLICATIONS

XP 002320817, "X-Tend™ 226, A Novel Ester with High Solubilizing Capacity", International Specialty Products, Aug. 2003.
French Search Report corresponding to FR 04/51417, issued on Mar. 14, 2005, 1 page.
Japanese Official Action dated Jan. 30, 2007 comments and Notice of Reasons for Rejection.
English translation of French Search Report for FR 04/51417.

*Primary Examiner*—Shelley A. Dodson
(74) *Attorney, Agent, or Firm*—Buchanan, Ingersoll & Rooney, PC

(57) ABSTRACT

The present invention relates to a process for photostabilizing, with respect to UV radiation, at least one dibenzoylmethane derivative with at least one arylalkyl benzoate derivative and at least one oil containing in its structure at least one amide unit.

Another subject of the invention also relates to a novel cosmetic or dermatological composition for topical use, characterized in that it comprises, in a cosmetically acceptable support:
(a) at least one UV-screening agent of the dibenzoylmethane derivative type and
(b) at least one arylalkyl benzoate derivative and
(c) at least one oil containing in its structure at least one amide unit.

The present invention also relates to the use of an arylalkyl benzoate derivative and an oil containing in its structure at least one amide unit in a cosmetic or dermatological composition comprising at least one dibenzoylmethane derivative, for the purpose of improving the stability with respect to UV rays of the said dibenzoylmethane derivative.

24 Claims, No Drawings

PHOTOSTABILIZATION OF DIBENZOYLMETHANE UV-SCREENING AGENTS WITH ARYLALKYL BENZOATE COMPOUNDS/AMIDE-BASED OILS AND PHOTOPROTECTIVE COMPOSITIONS COMPRISED THEREOF

CROSS-REFERENCE TO PRIORITY/PROVISIONAL APPLICATIONS

This application claims priority under 35 U.S.C. §119 (a)-(d) of FR 04/51417, filed Jul. 2, 2004, and claims benefit under 35 U.S.C. §119(e) of provisional application No. 60/589,010, filed Jul. 20, 2004, each hereby expressly incorporated by reference and each assigned to the assignee hereof.

CROSS-REFERENCE TO COMPANION APPLICATIONS

Copending applications Nos. 11/172,932 and 11/172,949, each filed concurrently herewith and each also assigned to the assignee hereof.

The present invention relates to a process for photostabilizing, with respect to UV radiation, at least one dibenzoylmethane derivative with at least one arylalkyl benzoate derivative and at least one oil containing in its structure at least one amide unit.

The invention also relates to novel compositions, in particular cosmetic compositions for topical use.

It is known that light radiation with wavelengths of between 280 nm and 400 nm permits tanning of the human epidermis and that light rays with wavelengths more particularly between 280 and 320 nm, known as UV-B rays, cause skin burns and erythema which can harm the development of a natural tan. For these reasons, as well as for aesthetic reasons, there is a constant demand for means of controlling this natural tanning in order thus to control the colour of the skin; this UV-B radiation should thus be screened out.

It is also known that UV-A rays, with wavelengths between 320 and 400 nm, which cause tanning of the skin, are liable to induce adverse changes therein, in particular in the case of sensitive skin or skin which is continually exposed to solar radiation. UV-A rays cause in particular a loss of elasticity of the skin and the appearance of wrinkles leading to premature ageing of the skin. They promote triggering of the erythemal reaction or amplify this reaction in certain individuals and may even be the cause of phototoxic or photoallergic reactions. Thus, for aesthetic and cosmetic reasons such as the conservation of the skin's natural elasticity, for example, an increasingly large number of people wish to control the effect of UV A rays on the skin. It in thus desirable also to screen out UV-A radiation.

For the purpose of protecting the skin and keratin materials against UV radiation, antisun compositions comprising organic screening agents that are active in the UV-A range and in the UV-B range are generally used. The majority of these screening agents are liposoluble.

In this respect, one particularly advantageous family of UV-A screening agents currently consists of dibenzoylmethane derivatives, and in particular 4-tert-butyl 4' methoxydibenzoylmethane, which have high intrinsic absorbing power. These dibenzoylmethane derivatives, which are products that are now well known per se as screening agents that are active in the UV-A range, are described in particular in French patent applications FR-A-2 326 405 and FR-A-2 440 933, as well as in European patent application EP-A-0 114 607; 4-tert-butyl-4'-methoxy-dibenzoylmethane is moreover currently sold under the trade mane "Parcol 1789" by the company Roche Vitamins.

Unfortunately, it has been found that dibenzoylmethane derivatives are products that are relatively sensitive to ultraviolet radiation (especially UV-A), i.e., more specifically, they have an annoying tendency to be degraded more or less quickly under the action of this UV. Thus, this substantial lack of photochemical stability of dibenzoylmethane derivatives towards ultraviolet radiation, to which they are by nature intended to be subjected, does not make it possible to ensure constant protection during prolonged exposure to the sun, and so the user must make repeated applications at regular and close time intervals in order to obtain effective protection of the skin against UV rays.

Dibenzoylmethane derivatives are oil-soluble solid screening agents. Among the oils capable of effectively dissolving these UV-screening agents, alkyl benzoates are known, especially C12/C15 alkyl benzoates, for instance the commercial products Finsolv TN or Witconol APM manufactured and sold by the company Witco.

However, the alkyl benzoates known hitherto do not solve the problem of the photostability of dibenzoylmethane derivatives with respect to UV radiation.

The Applicant has now discovered, surprisingly, that by combining the dibenzoylmethane derivatives mentioned above with an effective amount of an arylalkyl benzoate derivative and an oil containing in its structure at least one amide unit, it is possible to improve the photochemical stability (or photostability) of these same dibenzoylmethane derivatives, in a substantial and noteworthy manner.

This essential discovery forms the basis of the present invention.

Thus, in accordance with one of the subjects of the present invention, a process is now proposed for improving the stability of at least one dibenzoylmethane derivative with respect to UV radiation, which consists in combining the said dibenzoylmethane derivative with at least one arylalkyl benzoate derivative and at least one oil containing in its structure at least one amide unit.

The expression "oil containing in its structure at least one amide unit" will be understood throughout the text of the description to mean any compound comprising in its chemical structure at least one amide group (or function) of the type:

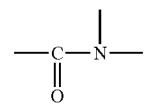

and simultaneously having the following characteristics:

a) liquid at 25° C., b) insoluble or immiscible in water at 25° C., c) no emulsifying properties.

Another subject of the invention also relates to a cosmetic or dermatological composition for topical use, characterized in that it comprises, in a cosmetically acceptable support:

(a) at least one UV-screening agent of the dibenzoylmethane derivative type and (b) at least one arylalkyl benzoate derivative and (c) at least one oil containing in its structure at least one amide unit.

Finally, a subject of the present invention is also the use of an arylalkyl benzoate derivative in a cosmetic or dermatological composition comprising at least one dibenzoylmethane derivative, for the purpose of improving the stability with respect to UV rays of the said dibenzoylmethane derivative.

Other characteristics, aspects and advantages of the invention will emerge on reading the detailed description that follows.

Among the dibenzoylmethane derivatives that may especially be mentioned, in a non-limiting manner, are:
2-methydibenzoylmethane
4-methyldibenzoylmethane
4-isopropyldibenzoylmethane
4-tert butyldibenzoylmethane
2,4-dimethyldibenzoylmethane
2,5-dimethyldibenzoylmethane
4,4' diisopropyldibenzoylmethane
4,4'-dimethoxydibenzoylmethane
4-tert-butyl-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl 4 tert-butyl-4'-methoxydibenzoylmethane.

Among the dibenzoylmethane derivatives mentioned above, 4-isopropyldibenzoylmethane will be used in particular, which is sold under the name "Eusolex 8020" by the company Merck, and corresponds to the following formula:

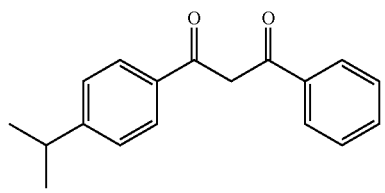

It is most particularly preferred to use 4-(tert-butyl)-4'-methoxydibenzoylmethane or Butyl Methoxy Dibenzoylmethane, sold under the trade name "Parsol 1789" by the company Roche Vitamins; this screening agent corresponds to the following formula:

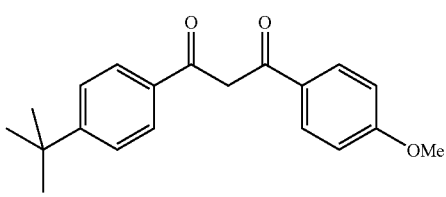

The dibenzoylmethane derivative(s) may be present in the compositions in accordance with the invention in contents preferably ranging from 0.01% to 10% by weight and more preferably from 0.1% to 6% by weight relative to the total weight of the composition.

The arylalkyl benzoate derivatives in accordance with the invention are preferably chosen from those of formula (I) or (II) below:

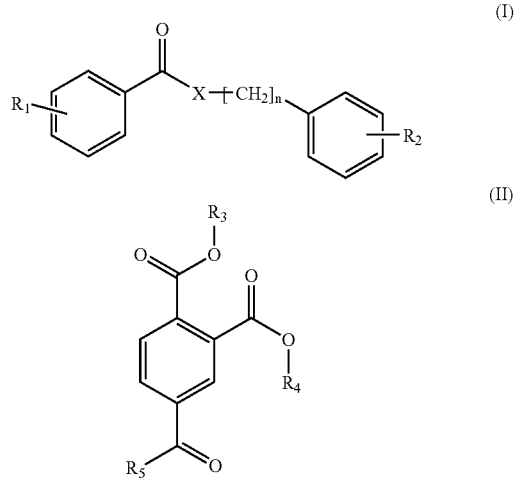

in which:
X denotes O, S or N;
n is an integer from 1 to 10 and more preferably from 2 to 6;
$R_1$ and $R_2$, which may be identical or different, denote a hydrogen atom; a hydroxyl group; a halogen atom (chlorine or fluorine); a linear or branched $C_1$-$C_4$ alkoxy radical (preferably methoxy or ethoxy); a nitro radical; an amino radical; a $C_6H_6SO_2$ radical; $R_3$, $R_4$ and $R_5$, which may be identical or different, denote a group of formula:

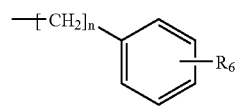

in which n has the same meaning indicated above; $R_6$ denotes a hydrogen atom; a hydroxyl group; a halogen atom (for example chlorine or fluorine); a linear or branched $C_1$-$C_4$ alkoxy radical (preferably methoxy or ethoxy); a nitro radical; an amino radical; a $C_6H_6SO_2$ radical.

The arylalkyl benzoate derivatives in accordance with the invention and the syntheses thereof have been known for a long time in the chemistry literature and especially in patent PL 55230.

Among the arylalkyl benzoate derivatives mentioned above, 2-ethyl phenyl benzoate will be used more particularly

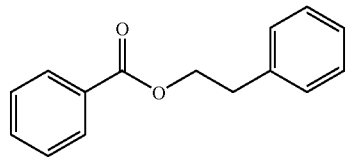

for instance the commercial product X-Tend 226®sold by the company ISP.

The arylalkyl benzoate derivatives in accordance with the invention may be present in the compositions in accordance with the invention in contents ranging from 0.1% to 40% by weight and more preferably from 0.1% to 30% by weight relative to the total weight of the composition.

The oil(s) having in their structure at least one amide unit in accordance with the invention is (are) preferably chosen from the compounds of formula (III) below:

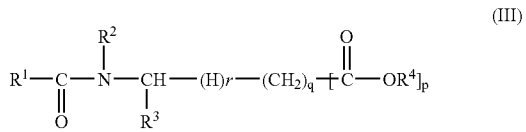

in which:
- the radical $R^1$ represents an optionally functionalized, aliphatic, cycloaliphatic or cyclic, saturated or unsaturated monovalent hydrocarbon-based radical containing from 1 to 30 carbon atoms and preferably from 1 to 22 carbon atoms, limits inclusive;
- the radicals $R^2$, $R^3$ and $R^4$, which may be identical or different, represent hydrogen or optionally functionalized, aliphatic, cycloaliphatic or cyclic, saturated or unsaturated monovalent hydrocarbon-based radicals containing from 1 to 30 carbon atoms and preferably from 1 to 22 carbon atoms, limits inclusive;
- r is 0 or 1;
- q is an integer from 0 to 2;
- p is 0 or 1, with the proviso that:
when p=1, then r is 0 and when p=0, then q=0 and r=1.

Examples of saturated aliphatic hydrocarbon-based radicals that may especially be mentioned include linear or branched, substituted or unsubstituted $C_1$-$C_{30}$ and preferably $C_1$-$C_{22}$ alkyl radicals, and in particular methyl, ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

Examples of saturated cyclic hydrocarbon-based radicals that may especially by mentioned include cyclopentyl and cyclohexyl radicals, which are optionally substituted, in particular with alkyl radicals.

Examples of unsaturated aliphatic hydrocarbon-based radicals that may especially be mentioned include linear or branched, substituted or unsubstituted, $C_2$-$C_{30}$ and preferably $C_2$-$C_{22}$ alkenyl or alkynyl radicals, and in particular vinyl, allyl, oleyl and linoleyl radicals.

Examples of unsaturated cyclic hydrocarbon-based radicals that may especially be mentioned in particular include aryl radicals such as phenyl and naphthyl, which are optionally substituted, in particular with alkyls, for instance a tolyl radical, and examples of unsaturated cycloaliphatic radicals that may be mentioned more particularly include benzyl and phenylethyl radicals.

The term "functionalized radicals" more particularly means radicals comprising in their chemical structure, either in the main chain or on a secondary chain unit, one or more functional groups especially such as esters, ethers, alcohols, amines, amides and ketones, but preferably esters.

The preferred amide-based oils of formula (II) are chosen from those in which:
- $R^1$ represents a linear or branched $C_2$-$C_{22}$ alkyl radical; a linear or branched $C_2$-$C_{22}$ alkenyl radical; an aryl radical;
- $R^2$ represents a hydrogen atom or a linear or branched $C_1$-$C_6$ alkyl group;
- $R^3$ represents a hydrogen atom or a linear or branched $C_1$-$C_6$ alkyl group;
- $R^4$ represents a linear or branched $C_2$-$C_{10}$ alkyl radical or a linear or branched $C_2$-$C_{10}$ alkenyl radical or a sterol residue.

In formula (III) presented above, the group $R^1(CO)$— is an acyl group of an acid preferably chosen from the group formed by acetic acid, toluic acid, capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids. These acids may also contain a hydroxyl group.

In formula (III), when p is 1, the portion —$N(R^2)CH(R^3)(CH_2)q(CO)$— of the amino acid ester is preferably chosen from those corresponding to the following amino acids:

glycine, alanine, valine, leucine, isoleucine, serine, threonine, proline, hydroxyproline, 3-alanine, N-butyl-β-alanine, aminobutyric acid, aminocaproic acid, sarcosine or N-methyl-β-alanine.

In formula (III), when p is 1, the portion of the amino acid esters corresponding to the group $OR^4$ may be obtained from alcohols chosen from the group formed by methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

The oils containing in their structure at least one amide function of formula (III) in accordance with the invention are known per se. Some of them are especially described with their methods of preparation in patent applications EP 1 044 676 and EP 0 928 608 from the company Ajinomoto Co. Others are known in cosmetics, for instance insect repellents such as ethyl N acetyl N butylaminopropionate or N,N diethyltolu amide.

Among the compounds of formula (III) that are particularly preferred, mention may be made of:

(1) N-acetyl-N-butylaminopropionate, having the following formula:

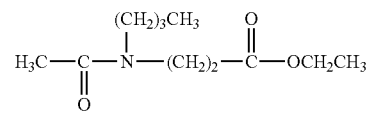

such as the product sold under the trade name Repellent R3535 by the company Merck;

(2) isopropyl N-lauroylsarcosinate of formula:

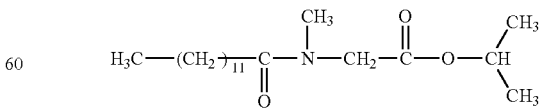

such as the product sold under the name Eldew SL-205 by the company Ajinomoto;

(3) N,N diethyltoluamide of formula:

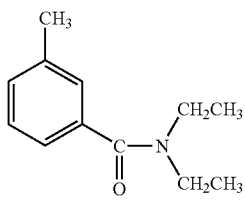

such as the product sold under the trade name Deet by the company Showa Denko.

The oil(s) containing in their structure at least one amide function as defined above is (are) present in the compositions according to the invention are in concentrations preferably ranging from 0.1% to 40% by weight and more preferably from 1% to 20% by weight relative to the total weight of the composition.

According to the present invention, the photostabilizing mixture of arylalkyl benzoate derivative/amide-based oil will be used in a sufficient amount for obtaining an appreciable and significant improvement in the photostability of the dibenzoylmethane derivative in a given composition. This minimum amount of photostabilizer to be used may vary according to the amount of dibenzoylmethane present at the start in the compound and according to the nature of the cosmetically acceptable support adopted for the composition. It may be determined without any difficulty by means of a standard test for measuring photostability.

The compositions in accordance with the invention may also comprise other additional UVA-active and/or UVB-active organic or mineral photoprotective agents that are water soluble or liposoluble or insoluble in the cosmetic solvents commonly used.

The additional organic photoprotective agents are chosen especially from anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in U.S. patent application Ser. No. 5,237,071, U.S. Pat. No. 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; dimers derived from α-alkylstyrene, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981, and mixtures thereof.

As examples of additional organic photoprotective agents, mention may be made of those denoted hereinbelow under their INCI name:

para Aminobenzoic acid derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF.

Salicylic derivatives:
Homosalate sold under the name "Eusolex HMS" by Rona/EM industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

Cinnamic derivatives:
Ethylhexyl methoxycinnamate sold in particular under the trade name "Parsol MCX" by Hoffmann LaRoche,
Isopropyl methoxycinnamate,
Isoamyl methoxycinnamate sold under the trade name "Neo Heliopan E 1000" by Haarmann and Reimer,
Cinoxate,
DEA methoxycinnamate,
Diisopropyl methylcinnamate,
Glyceryl ethylhexanoate dimethoxycinnamate.

β,β-Diphenylacrylate derivatives:
Octocrylene sold in particular under the trade name "Uvinul N539" by BASF,
Etocrylene sold in particular under the trade name "Uvinul N35" by BASF.

Benzophenone derivatives:
Benzophenone-1 sold under the trade name "Uvinul 400" by BASF,
Benzophenone-2 sold under the trade name "Uvinul D50" by BASF,
Benzophenone-3 or Oxybenzone sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF,
Benzophenone-12
n-hexyl 2-(4-diethylamino-2-hydroxybenzoyl)benzoate.

Benzylidenecamphor derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole derivatives:
Phenylbenzimidazolesulfonic acid sold in particular under the trade name "Eusolex 232" by Merck,
Disodium phenyl dibenzimidazole tetrasulfonate sold under the trade name "Neo Heliopan AP" by Haarmann and Reimer.

Phenylbenzotriazole derivatives:
Drometrizole trisiloxane sold under the name "Silatrizole" by Rhodia Chimie, Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals.

Triazine derivatives:
Bis-Ethylhexyloxyphenol Methoxyphenyl Triazine sold under the trade name "Tinosorb S" by Ciba Geigy,
Ethylhexyltriazone sold in particular under the trade name "Uvinul T150" by BASF,
Diethylhexylbutamidotriazone sold under the trade name "Uvasorb HEB" by Sigma 3V,
2,4,6-tris(diisobutyl 4'-aminobenzalmalonate)-s-triazine.

Anthranilic derivatives:
Menthyl anthranilate sold under the trade name "Neo Heliopan MA" by Haarmann and Reimer.

Imidazoline derivatives:
Ethylhexyldimethoxybenzylidenedioxoimidazonline propionate.

Benzalmalonate derivatives:
Polyorganosiloxane containing benzalmalonate functions, for instance Polysilicone-15, sold under the trade name "Parsol SLX" by Hoffman LaRoche.

4,4-Diarylbutadiene derivatives:
1,1-Dicarboxy(2,2' dimethylpropyl)-,4,4-diphenyl-butadiene Benzoxazole derivatives:
2,4-bis[5-(1-dimethylpropyl)benzoxazol-2-yl(4-phenyl)imino]-6-(2-ethylhexyl)imino-1,3,5-triazine sold under the name Uvasorb K2A by Sigma 3V and mixtures thereof.

The preferred additional organic photoprotective agents are chosen from:
Ethylhexyl Methoxycinnamate,
Homosalate,
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydoxybenzoyl)benzoate,
4 Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Ethylhexyl Triazone,
Bis-Ethylhexyloxyphenol Methoxyphenyl Triazine,
Diethylhexyl Butamido Triazone,
Drometrizole trisiloxane,
Polysilicone-15,
1,1-Dicarboxy(2,2'-dimethylpropyl)-4,4-diphenyl butadiene,
2,4-Bis[5-1(dimethylpropyl)benzoxazol-2-yl(4-phenyl)imino]-6-(2-ethylhexyl)imino-1,3,5-triazine, and mixtures thereof.

The additional mineral photoprotective agents are chosen from pigments and been more preferably nanopigments (mean size of the primary particles: generally between 5 nm and 100 nm and preferably between 10 nm and 50 nm) of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen or elastin), alkanolamines, silicon oxides, metal oxides, sodium hexametaphosphate, alumina of glycerol.

The treated nanopigments may more particularly be titanium oxides treated with:
silica and alumina, such as the products "Microtitanium Dioxide MT 500 SA" and "Microtitanium dioxide MT 100 SA" from the company Tayca, and the products "Tioveil Fin", "Tioveil OP", "Tioveil MOTG" and "Tioveil IPM" from the company Tioxide,
alumina and aluminium stearate, such as the product "Microtitanium Dioxide MT 100 T" from the company Tayca,
alumina and aluminium laurate, such as the product "Microtitanium Dioxide MT 100 S" from the company Tayca,
iron oxides and iron stearate, such as the product "Microtitanium Dioxide MT 100 F" from the company Tayca,
silica, alumina and silicone, such as the products "Microtitanium Dioxide MT 100 SAS", "Microtitanium Dioxide MT 600 SAS" and "Microtitanium Dioxide MT 500 SAS" from the company Tayca,
sodium hexametaphosphate, such as the product "Microtitanium Dioxide MT 150 W" from the company Tayca,
octyltrimethoxysilane, such as the product "T-805" from the company Degussa,
alumina and stearic acid, such as the product "UVT-M160" from the company Kemira,
alumina and glycerol, such as the product "UVT-M212" from the company Kemira,
alumina and silicone, such as the product "UVT-M262" from the company Kemira.

Other titanium oxide nanopigments treated with a silicone are preferably $TiO_2$ treated with octyltrimethylsilane and for which the mean size of the elementary particles in between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile $TiO_2$ treated with a polydimehtylhydrogenosiloxane and for which the mean size of the elementary particles is 25 nm, such as the product sold under the trade name "Microtitanium Dioxide USP Grade Hydrophobic" by the company Color Techniques.

The uncoated titanium oxide nanopigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide nanopigments are, for example:
those sold under the name "Z-Coto" by the company Sunsmart;

those sold under the name "Nanox" by the company Elementis;

those sold under the name "Nanogard WCD 2025" by the company Nanophase Technologies.

The coated zinc oxide nanopigments are, for example:

those sold under the name "Zinc Oxide CS-5" by the company Toshibi (ZnO coated with polymethylhydrogenosiloxane);

those sold under the name "Nanogard Zinc Oxide FN" by the company Nanophase Technologies (as a 40% dispersion in Finsolv TN, $C_{12}$-$C_{15}$ alkyl benzoate);

those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane);

those sold under the name "NFD Ultrafine ZNO" by the company Daikin (ZnO coated with perfluoroalkyl phosphate and copolymer based on perfluoroalkylethyl as a dispersion in cyclopentasiloxane);

those sold under the name "SPD-Z1" by the company Shin-Etsu (ZnO coated with silicone-grafted acrylic polymer, dispersed in cyclodimethylsiloxane);

those sold under the name "Escalol Z100" by the company ISP (alumina-treated ZnO dispersed in an ethylhexyl methoxycinnamate/PVP-hexadocene/methicone copolymer mixture);

those sold under the name "Fuji ZNO-SMS-10" by the company Fuji Pigment (ZnO coated with silica and polymethylsilsesquioxane);

those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide nanopigments are sold under the name "Colloidal Cerium Oxide" by the company Rhone-Poulene.

The uncoated iron oxide nanopigments are sold, for example, by the company Arnaud under the names "Nanogard WCD 2002 (FE 45B)", "Nanogard Iron FE 45 BL AQ", "Nanogard FE 45R AQ" and "Nanogard WCD 2006 (FE 45R)" or by the company Mitsubishi under the name "TY-220".

The coated iron oxide nanopigments are sold, for example, by the company Arnard under the names "Nanogard WCD 2008 (FE 45B FN)", "Nanogard WCD 2009 (FE 45B 556)", "Nanogard FE45 BL 345" and "Nanogard FE 45 BL" or by the company BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The nanopigments may be introduced into the compositions according to the invention in unmodified form or in the form of pigmentary paste, i.e. as a mixture with a dispersant, as described, for example, in document GB-A 2 206 339.

The additional photoprotective agents are generally present in the compositions according to the invention in proportions ranging from 0.01% to 20% by weight relative to the total weight of the composition and preferably ranging from 0.1% to 10% by weight relative to the total weight of the composition.

The compositions according to the invention may also contain agents for artificially tanning and/or browning the skin (self-tanning agents) and more particularly dihydroxyacetone (DHA). They are preferably present in amounts ranging from 0.1% to 10% by weight relative to the total weight of the composition.

The compositions in accordance with the present invention may also comprise standard cosmetic adjuvants chosen especially from fatty substances, organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents or any other ingredient usually used in cosmetics and/or dermatology.

The fatty substances may consist of an oil or a wax or mixtures thereof. The term "oil" means a compound that is liquid at room temperature. The term "wax" means a compound that is solid or substantially solid at room temperature and whose melting point is generally greater than 35° C.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters (for instance the $C_{12}$-$C_{15}$ alkyl benzoate sold under the trade name "Finsolv TN" by the company Witco, octyl palmitate, isopropyl lanolate and triglycerides, including capric/caprylic acid triglycerides), oxyethylenated or oxyproplyenated fatty esters and ethers; silicone oils (cyclomethicone and polydimethylsiloxanes, or PDMS) or fluoro oils, and polyalkylenes.

Waxy compounds that may be mentioned include paraffin, cernauba wax, beeswax and hydrogenated castor oil.

Among the organic solvents that may be mentioned are lower alcohols and polyols. These polyols may be chosen from glycols and glycol ethers, for instance ethylene glycol, propylene glycol, butylene glycol, dipropylene glycol or diethylene glycol.

Hydrophilic thickeners that may be mentioned include carboxyvinyl polymers such as the Carbopol products (carbomers) and the Pemulen products (acrylate C10-C30-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally crosslinked and/or neutralized, for instance the poly(2-acrylamido-2-methylpropanesulfonic acid) sold by the company Hoechst under the trade name "Hostacerin AMPS" (CTFA name: ammonium polyacryldimethyltauramide); cellulose based derivatives such as hydroxyethylcellulose; polysaccharides and especially gums such as xanthan gum; and mixtures thereof.

Lipophilic thickeners that may be mentioned include modified clays such as hectorite and its derivatives, for instance the products sold under the name bentone.

Among the active agents that may be mentioned are:
antipollution agents and/or free-radical scavengers;
depigmenting agents and/or propigmenting agents;
antiglycation agents;
NO-synthase inhibitors;

agents for stimulating the synthesis of dermal or epidermal macromolecules and/or for preventing their degradation;

agents for stimulating fibroblast proliferation;

agents for stimulating keratinocyte proliferation;

muscle relaxants;

tensioning agents;

desquamating agents;

moisturizers;

anti-inflammatory agents;

agents acting on the energy metabolism of cells;

insect repellents;

substance P or CGRP antagonists.

Needless to say, a person skilled in the art will take care to select the optional additional compound(s) mentioned above and/or the amounts thereof such that he advantageous properties intrinsically associated with the compounds in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion, a powder or a solid tube, and may optionally be packaged as an aerosol and may be in the form of a mousse or a spray.

The compositions according to the invention are preferably in the form of an oil-in-water or water-in-oil emulsion.

The emulsion generally contain at least one emulsifier chosen from amphoteric, anionic, cationic and nonionic emulsifiers, which are used alone or as a mixture. The emulsifiers are appropriately chosen according to the emulsion to be obtained (W/O or O/W).

As emulsifying surfactants that may be used for the preparation of the W/O emulsions, examples that may be mentioned include sorbitan, glycerol or sugar alkyl esters or ethers; silicon surfactants, for instance dimethicone copolyols, such as the mixture of cyclomethicone and of dimethicone copolyol, sold under the name "DC 5225 C" by the company Dow Corning, and alkyldimethicone copolyols such as laurylmethicone copolyol sold under the name "Dow Corning 5200 Formulation Aid" by the company Dow Corning; cetyl-dimethicone copolyol, such as the product sold under the name Abil EM 90R by the company Goldschmidt, and the mixture of cetyldimethicon copolyol, of poly-glycerol isostearate (4 mol) and of hexyl laurate, sold under the name Abil WE O9 by the company Goldschmidt. One or more co-emulsifiers may also be added thereto, which may be chosen advantageously from the group comprising polyol alkyl esters. Polyol alkyl esters that may especially be mentioned include glycerol and/or sorbitan esters, for example polyglyceryl isostearate, such as the product sold under the name Isolan GI 34 by the company Goldschmidt, sorbizan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkly ethers; sugar esters, for instance sucrose stearate; fatty alkyl ethers of sugars, especially alkylpolyglucosides (APG) such as decylglucoside and laurylglucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name MonLanov 202 by the company SEPPIC. According to one particular embodiment of the invention, the mixture of the alkylpolyglucoside as defined above with the corresponding fatty alcohol may be in the form of a self-emulsifying composition as described, for example, in document WO-A-92/06778.

When it is an emulsion, the aqueous phase of this emulsion may comprises a nonioinc vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention consists of the use of the compositions according to the invention as defined above for the manufacture of cosmetic products for treating the skin, the lips, the nails, the hair, the eyelashes, the eyebrows and/or the scalp, especially care products and makeup products.

The cosmetic compositions according to the invention may be used, for example, as care products and/or antisun products for the face and/or the body, of liquid to semi-liquid consistency, such as milks, more or less rich creams, cream-gels and pastes. They may optionally be packaged as an aerosol and may be in the from of mousses or sprays.

The compositions according to the invention in the form of vaporizable fluid lotions in accordance with the invention are applied to the skin or the hair in the form of fine particles by means of pressurization devices. The devices in accordance with the invention are well known to those skilled in the are and include non-aerosol pumps or "atomizers", aerosol containers comprising a propellant and also aerosol pumps using compressed air as propellant. The latter pumps are described in U.S. Pat. No. 4,077,441 and U.S. Pat. No. 4,850,517 (forming an integral part of the content of the description).

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

Concrete but in no way limiting examples illustrating the invention will now be given.

The following antisun formulations were prepared; the amounts are indicated in percentages by weight:

| Compositions | Example 1 (invention) | Example 2 (invention) |
|---|---|---|
| PHASE A: | | |
| Polydimethylsiloxane | 0.5 | 0.5 |
| Preservatives | 1.0 | 1.0 |
| Stearic acid | 1.5 | 1.5 |
| Glyceryl monostearate/PEG stearate mixture (100 EO) | 1.0 | 1.0 |
| Cetylstearyl glucoside/cetylstearyl alcohol mixture | 2.0 | 2.0 |
| Cetyl alcohol | 0.5 | 0.5 |
| Butylmethoxydibenzoylmethane | 2.0 | 2.0 |
| 2-Phenylethyl benzoate (X-Tend 226 from ISP) | 10 | 10 |
| N-Lauroyl isopropyl sarcosinate (Eldew SL-205 - Ajinomoto) | 10 | — |
| Ethyl N-butyl-N-acetylaminopropionate (R3535 from Merck) | — | 10 |
| PHASE B: | | |
| Deionized water | qs 100 | qs 100 |
| Sequestering agent | 0.1 | 0.1 |
| Glycerol | 5.0 | 5.0 |
| Xanthan gum | 0.2 | 0.2 |
| Monocetyl phosphate | 1.0 | 1.0 |
| PHASE C: | | |
| Isohexadecane | 1.0 | 1.0 |
| Acrylic acid/stearyl methacrylate copolymer | 0.2 | 0.2 |
| Triethanolamine | qs | qs |

The aqueous phase (Phase B) containing all of its ingredients is heated to 80° C. on a water bath. The fatty phase (Phase A) containing all of its ingredients is heated to 80° C. on a water bath. A is emulsified in B with stirring of rotor-stator type (machine from the company Moritz). Phase C is incorporated and the mixture is allowed to cool to room temperature with moderate stirring. The triethanolamine is introduced so as to adjust the pH to the desired value at the end of manufacture.

What is claimed is:

1. A topically applicable, photostable cosmetic/dermatological photoprotective composition, comprising an effective UV-photoprotecting amount of at least one dibenzoylmethane UV-screening agent, and, as a stabilizing admixture therefor, a thus effective amount of at least one arylalkyl benzoate compound and at least one amide-based oil, formulated into a topically applicable, cosmetically/dermatologically acceptable medium.

2. The cosmetic/dermatological composition as defined by claim 1, said at least one dibenzoylmethane UV-screening agent being selected from the group consisting of:
   2-methyldibenzoylmethane;
   4-methyldibenzoylmethane;
   4-isopropyldibenzolylmethane;
   4-tert-butyldibenzoylmethane;
   2,4-dimethyldibenzoylmethane;
   2,5-dimethyldibenzoylmethane;
   4,4'-diisopropyldibenzoylmethane;
   4,4'-dimethoxydibenzoylmethane;
   4-tert-butyl-4'-methoxydibenzoylmethane;
   2-methyl-5-isopropyl-4'-methoxydibenzoylmethane;
   2-methyl-5-tert-butyl-4'-methoxydibenzoylmethane;
   2,4-dimethyl-4'-methoxydibenzoylmethane, and
   2,6-dimethyl-4-tert-butyl-4'-methoxydibenzoylmethane.

3. The cosmetic/dermatological composition as defined by claim 1, said at least one dibenzoylmethane UV-screening agent comprising 4-(tert-butyl)-4'-methoxydibenzoylmethane or Butyl Methoxy Dibenzoylmethane.

4. The cosmetic/dermatological composition as defined by claim 1, said at least one arylalkyl benzoate compound having the formula (I) or (II) below:

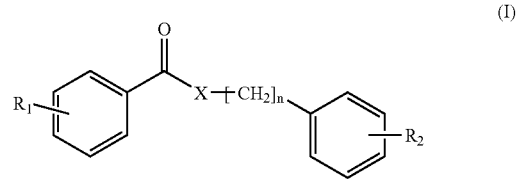

(I)

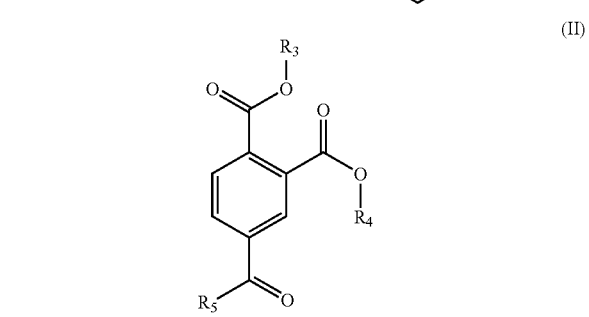

(II)

in which:

X is O, S or N;

n is an integer ranging from 1 to 10;

$R_1$ and $R_2$, which may be identical or different, are each a hydrogen atom, a hydroxyl group, a halogen atom, a linear or branched $C_1$-$C_4$ alkoxy radical, a nitro radical, an amino radical, or a $C_6H_6SO_2$ radical;

$R_3$, $R_4$ and $R_5$, which may be identical or different, are each a radical of formula:

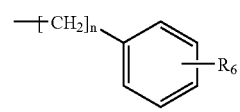

in which n has the same definition indicted above, and $R_6$ is a hydrogen atom, a hydroxyl group, a halogen atom, a linear or branched $C_1$-$C_4$ alkoxy radical, a nitro radical, an amino radical, or a $C_6H_6SO_2$ radical.

5. The cosmetic/dermatological composition as defined by claim 4, said at least one arylalkyl benzoate compound comprising 2-phenylethyl benzoate of formula:

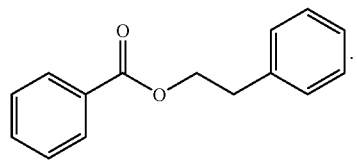

6. The cosmetic/dermatological composition as defined by claim 1, said at least one amide-based oil having the formula (III) below:

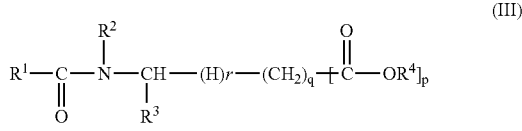
(III)

in which:
the radical R¹ is an optionally functionalized, aliphatic, cycloaliphatic or cyclic, saturated or unsaturated monovalent hydrocarbon-based radical having from 1 to 30 carbon atoms;
the radicals R², R³ and R⁴, which may be identical or different, are each hydrogen or optionally functionalized, aliphatic, cycloaliphatic or cyclic, saturated or unsaturated monovalent hydrocarbon-based radicals having from 1 to 30 carbon atoms;
r is 0 or 1;
q is an integer ranging from 0 to 2;
p is 0 or 1;
with the proviso that:
when p=1, then r is 0 and when p=0, then q=0 and r=1.

7. The cosmetic/dermatological composition as defined by claim 6, wherein formula (III):
R¹ is a linear or branched $C_1$-$C_{22}$ alkyl radical, a linear or branched $C_2$-$C_{22}$ alkenyl radical, or an aryl radical;
R² is a hydrogen atom or a linear or branched $C_1$-$C_6$ alkyl radical;
R³ is a hydrogen atom or a linear or branched $C_1$-$C_6$ alkyl radical; and
R⁴ is a linear or branched $C_1$-$C_{10}$ alkyl radical, a linear or branched $C_2$-$C_{10}$ alkenyl radical, or a sterol residue.

8. The cosmetic/dermatological composition as defined by claim 7, in which the oil of formula (III) is selected from among those in which the group R¹(CO)— is an acyl group of an acid selected from the group consisting of acetic acid, toluic acid, capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids; these acids may also contain a hydroxyl group.

9. The cosmetic/dermatological composition as defined by claim 7, in which the oil of formula (III) is selected from among those in which p is 1 and the moiety —N(R²)CH(R³)(CH₂)q(CO)— of the amino acid ester is selected from the group consisting of the following amino acids:
glycine, alanine, valine, leucine, isoleucine, serine, threonine, proline, hydroxyproline, β-alanine, N-butyl-β-alanine, aminobutyric acid, aminocaproic acid, sarcosine and N-methyl-β-alanine.

10. The cosmetic/dermatological composition as defined by claim 7, in which the oil of formula (III) is selected from among those in which p is 1 and the moiety of the amino acid esters corresponding to the group OR⁴ is obtained from alcohols selected from the group consisting of methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

11. The cosmetic/dermatological composition as defined by claim 1, said at least one amide-based oil comprising:

ethyl-N-acetyl-N-butylaminopropionate, having the following formula:

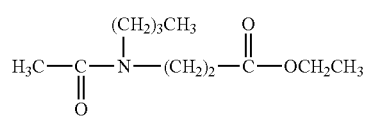

isopropyl N-lauroylsarcosinate of formula:

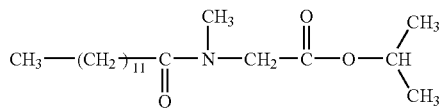

or N,N-diethyltoluamide of formula:

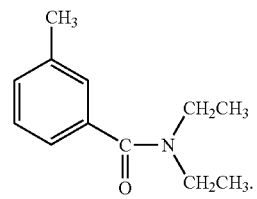

12. The cosmetic/dermatological composition as defined by claim 1, said at least one dibenzoylmethane UV-screening agent comprising from 0.01% to 10% by weight thereof.

13. The cosmetic/dermatological composition as defined by claim 1, said at least one amide-based oil comprising from 0.1% to 40% by weight thereof.

14. The cosmetic/dermatological composition as defined by claim 1, further comprising at least one other UV-A-active and/or UV-B-active organic or mineral photoprotective agent that is water-soluble or liposoluble or insoluble in the cosmetic solvents commonly employed.

15. The cosmetic/dermatological composition as defined by claim 14, comprising at least one additional organic photoprotective agent selected from among anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene derivatives; 4,4-diarylbutadienes, and mixtures thereof.

16. The cosmetic/dermatological composition as defined by claim 15, comprising at least one organic UV-screening agent selected from among the following compounds:
Ethylhexyl Methoxycinnamate,
Homosalate,
Ethylhexyl salicylate,
Octocrylene,
Phenylbenzimidazolesuflonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid, Disodium phenyldibenzimidazoletetrasulfonate,
Methylenebis(benzotriazole)tetramethylbutylphenol,
Ethylhexyl Triazine,
Bis-Ethylhexyloxyphenol Methoxyphenyl Triazine,
Diethylhexyl Butamido Triazine,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl) imino]-6-(2-ethylhexyl)imino-1,3,5-triazine,
and mixtures thereof.

17. The cosmetic/dermatological composition as defined by claim 14, comprising at least one additional mineral photoprotective agent which comprises treated or untreated metal oxide pigments or nanopigments.

18. The cosmetic/dermatological composition as defined by claim 17, comprising pigments or nanopigments selected from among titanium oxide, zinc oxide, iron oxide, zirconium oxide and cerium oxide, and mixtures thereof, which are treated or untreated.

19. The cosmetic/dermatological compositions as defined by claim 1, further comprising at least one agent for artificially tanning and/or browning the skin.

20. The cosmetic/dermatological composition as defined by claim 1, further comprising at least one adjuvant selected from among fatty substances, organic solvents, ionic or nonionic, hydrophilic or lipophilic thickeners, softeners, humectants, opacifiers, stabilizers, emollients, silicones, anti-foams, fragrances, preservatives, anionic, cationic, nonionic, zwitterionic or amphoteric surfactants, active agents, fillers, polymers, propellants and acidifying or basifying agents.

21. A regime or regimen for cosmetically treating or caring for the skin, lips, nails, hair, eyelashes, eyebrows and/or scalp of an individual in need of such treatment, comprising topically applying thereon, a thus effective amount of the cosmetic/dermatological composition as defined by claim 1.

22. A regime or regimen for photoprotecting the skin, hair, lips and/or scalp against the damaging effects of UV-irradiation, comprising topically applying thereon, a thus effective amount of the cosmetic/dermatological composition as defined by claim 1.

23. A process for enhancing the stability with respect to UV-irradiation of at least one dibenzoylmethane UV-screening agent, comprising formulating therewith a thus effective amount of at least one arylalkyl benzoate compound and at least one amide-based oil.

24. The cosmetic/dermatological composition as defined by claim 1, formulated as an emulsion, a milk, a gel, a cream, a lotion, a powder, a stick, a mousse, or a spray.

* * * * *